United States Patent
Korn et al.

(10) Patent No.: US 9,945,882 B2
(45) Date of Patent: Apr. 17, 2018

(54) METHOD FOR PIPETTING LIQUIDS IN AN AUTOMATED ANALYSIS APPARATUS

(71) Applicant: Siemens Healthcare Diagnostics Products GmbH, Marburg (DE)

(72) Inventors: Matthias Korn, Nastaetten (DE); Kristin Moser, Kelkheim (DE); Holger Pufahl, Liederbach (DE); David Solbach, Frankfurt (DE); Christian Verhalen, Wiesbaden (DE)

(73) Assignee: Siemens Healthcare Diagnostics Products GmbH, Marburg (DE)

(*) Notice: Subject to any disclaimer, the term of this patent is extended or adjusted under 35 U.S.C. 154(b) by 163 days.

(21) Appl. No.: 15/208,392

(22) Filed: Jul. 12, 2016

(65) Prior Publication Data
US 2017/0016927 A1    Jan. 19, 2017

(30) Foreign Application Priority Data
Jul. 13, 2015    (EP) .................................... 15176410

(51) Int. Cl.
*G01N 35/10* (2006.01)
*G01F 23/26* (2006.01)

(52) U.S. Cl.
CPC ....... *G01N 35/1016* (2013.01); *G01F 23/263* (2013.01); *G01N 35/1004* (2013.01); *G01N 35/1011* (2013.01); *G01N 2035/1018* (2013.01); *G01N 2035/1025* (2013.01)

(58) Field of Classification Search
CPC ........... G01N 35/1016; G01N 35/1004; G01N 35/1011; G01N 2035/1018; G01N 2035/1025; G01F 23/263
See application file for complete search history.

(56) References Cited

U.S. PATENT DOCUMENTS

| | | | | |
|---|---|---|---|---|
| 4,502,126 A | * | 2/1985 | Mizoguchi | G01F 23/00 222/23 |
| 5,012,683 A | * | 5/1991 | Davis | G01F 23/263 73/290 R |
| 5,319,954 A | * | 6/1994 | Koeda | G01N 35/1016 73/19.1 |
| 2009/0316519 A1 | * | 12/2009 | Gorka | B01F 3/0865 366/140 |
| 2010/0104478 A1 | * | 4/2010 | Kondou | B01L 3/527 422/400 |

(Continued)

FOREIGN PATENT DOCUMENTS

| | | |
|---|---|---|
| EP | 0526210 | 2/1993 |
| EP | 0990907 | 4/2000 |
| EP | 2172782 | 4/2010 |

(Continued)

OTHER PUBLICATIONS

European Search Report of European Application No. 15176410.7-1553 dated Feb. 8, 2016.

*Primary Examiner* — Ryan Walsh
(74) *Attorney, Agent, or Firm* — Dugan & Dugan, PC

(57) ABSTRACT

ABSTRACT The present invention lies in the field of automated analysis apparatuses and relates to a method for transferring a liquid volume from a first liquid vessel into a second liquid vessel. The method ensures increased pipetting accuracy, even from liquid vessels which have foam on the surface of the liquid.

16 Claims, 1 Drawing Sheet

(56) References Cited

U.S. PATENT DOCUMENTS

2013/0065797 A1* 3/2013 Silbert ............... G01N 35/0099
506/39

FOREIGN PATENT DOCUMENTS

| EP | 2293083 | 3/2011 |
| --- | --- | --- |
| EP | 2561929 | 2/2013 |
| WO | WO 2011091245 | 7/2011 |
| WO | WO 2015066342 | 5/2015 |

* cited by examiner

METHOD FOR PIPETTING LIQUIDS IN AN AUTOMATED ANALYSIS APPARATUS

CROSS REFERENCE TO RELATED APPLICATION

This claims priority to European Patent Application No. EP 15176410.7, filed Jul. 13, 2015, which is hereby incorporated by reference herein in its entirety for all purposes.

FIELD

The present invention lies in the field of automated analysis apparatuses and relates to a method for transferring a liquid volume from a first liquid vessel into a second liquid vessel.

BACKGROUND

Current analysis apparatuses, as are routinely used in analytics, forensics, microbiology and clinical diagnostics, are able to carry out a multiplicity of detection reactions and analyses with a multiplicity of samples. In order to be able to carry out a multiplicity of tests in an automated manner, various automatically operating devices for the spatial transfer of measurement cells, reaction containers and reagent liquid containers are required, e.g., transfer arms with gripper functions, transport belts or rotatable transport wheels, and also devices for transferring liquids, e.g., pipetting devices. The apparatuses comprise a central control unit which, by means of appropriate software, is able, in a largely autonomous manner, to plan and work through the work steps for the desired analyses.

Many of the analysis methods used in such analysis apparatuses operating in an automated manner are based on optical methods. Measurement systems based on photometric (e.g. turbidimetric, nephelometric, fluorometric or luminometric) or radiometric measurement principles are particularly widespread. These methods permit the qualitative and quantitative detection of analytes in liquid samples without having to provide additional separation steps. The determination of clinically relevant parameters, for example the concentration or the activity of an analyte, is often carried out by an aliquot of a bodily fluid of a patient being mixed simultaneously or in succession with one or more test reagents in a reaction vessel, as a result of which a biochemical reaction is set in motion, which brings about a measurable change in an optical property of the test preparation.

The measurement result is in turn forwarded to a storage unit by the measurement system and evaluated. Subsequently, the analysis apparatus supplies a user with sample-specific measurement values by way of an output medium, e.g., a monitor, a printer or a network connection.

Sample liquids or reagent liquids are usually transferred by means of automated pipetting devices. Such pipetting devices generally comprise a height-adjustable pipetting needle which is arranged vertically on a displaceable or pivotable transfer arm and which is connected to a pump unit such that a desired volume of a liquid can be taken from a container by way of the pipetting needle and discharged into a target container at a different location. Usually, the pipetting needle is displaced to a position over a liquid container with the aid of the transfer arm and then lowered into the liquid container and into the liquid contained therein. Once the desired volume has been removed, the pipetting needle is driven upward and then driven to the desired target position over a liquid container, for example, over a measurement cell, with the aid of the transfer arm. There, the pipetting needle is lowered again, and the quantity of liquid is discharged.

It is conventional to equip pipetting devices with a fill-level sensor. The purpose of this is, firstly, to be able to determine the fill level of reagent liquids in reagent liquid containers during the operation of the automated analysis apparatus and report this to the control unit. This ensures, for example, that a user can be informed in good time about the necessary replacement of a reagent container. Secondly, determination of the fill level ensures that the pipetting needle is always immersed sufficiently deeply into the liquid to be removed, in order to avoid air being sucked in instead of liquid.

The most common method for determining the fill level is the determination of the fill level by capacitive means. To this end, the pipetting needle consists of an electrically conductive material and thus in principle forms the measurement electrode, and it furthermore comprises a reference electrode. The fill level can be determined continuously from the change in the electric capacitance between the pipetting needle and the reference electrode. Another method entails determining the fill level by optical means. To this end, the pipetting needle comprises an optoelectronic fill-level sensor consisting of a light source and a light sensor. In the case of immersion, the light is refracted by the liquid and it no longer reaches the light sensor, or it only reaches the latter in attenuated form. The fill level can be determined from the attenuation of the light signal.

A problem is that foam can form on the liquid surface in individual liquid containers. Liquid foam, i.e., air bubbles surrounded by liquid, often arises in surfactant-containing reagent liquids or also if, when pipetting a liquid volume, it is not only liquid but also air that is taken up and is discharged into a target container. The presence of foam on the liquid surface makes it difficult to determine the fill level of the liquid, since the foam is already detected as liquid upon immersion of a pipetting needle equipped with a fill-level sensor. This usually has the effect of detecting a false fill level that is too high, which in turn has the consequence that, upon removal of liquid, at least part of the volume that is sucked in consists of foam. This leads to pipetting inaccuracies, which ultimately lead to incorrect measurement results.

Various approaches for the avoidance of pipetting inaccuracies as a consequence of foam formation are known in the prior art.

EP-A1-0526210 describes a method in which, by means of a pipetting needle equipped with a fill-level sensor, the fill level in a reagent liquid container is determined before and after the suctioning of a liquid volume. If the change in the fill level in relation to a previously fixed value is abnormal, this indicates the presence of foam.

EP-A1-0990907 describes another method in which, by means of a pipetting needle equipped with a fill-level sensor, a continuous determination of the fill level is carried out during the immersion of the needle, and a logic unit is used to determine whether foam is present and, if yes, measures are introduced such that the liquid surface is detected under the foam.

A disadvantage is that, in order to avoid pipetting inaccuracies, liquid containers in which foam was detected trigger an alarm or a warning in the automated analysis apparatus or are automatically excluded from further removal of liquid. This has the effect that analyses cannot be carried out and that, in some cases, a user needs to replace the liquid container.

A further problem is that, by movement of liquid containers, liquid residues can adhere to the inner wall of the container above the liquid surface, resulting in a container with a fill level that is initially too low.

SUMMARY

Therefore, in the automatic transfer of liquid volumes in an automated analysis apparatus, the object of the present invention is to avoid pipetting inaccuracies and, particularly in cases where an implausible fill level of a liquid is measured, to nevertheless permit, by simple and cost-effective means, a precise removal of liquid, such that it is possible to do without an immediate alarm or a replacement of the liquid container.

According to the invention, the object is achieved by the fact that, if an implausible fill level of a liquid is measured upon immersion of a pipetting needle into the liquid, the pipetting needle is withdrawn from the liquid, without sucking in a liquid volume, and is then immersed again. This procedure can be repeated several times. It has been observed that, by the repeated immersion and withdrawal of the pipetting needle, foam located in the liquid container is broken up and, at least in cases where the implausible fill level is attributable to foam, a precise removal of liquid is therefore permitted. It is particularly advantageous that the method according to the invention can be implemented in a particularly simple and cost-effective manner, for example, in the form of corresponding control software, on any conventional automated analysis apparatus that has an automated pipetting device with integrated fill-level sensor.

The subject matter of the present invention is therefore a method for transferring a liquid volume from a first liquid vessel into a second liquid vessel, wherein a pipetting needle is used which is secured on an automatically displaceable or pivotable transfer arm and which has a fill-level sensor. The method comprises the steps:

a) immersing the pipetting needle into the liquid contained in the first liquid vessel, and measuring the fill level;
b) comparing the measured fill level with a predefined minimum fill level and a predefined maximum fill level;
c) determining that the measured fill level
   i. exceeds the predefined maximum fill level or
   ii. is below the predefined maximum fill level and exceeds the predefined minimum fill level or
   iii. is below the predefined minimum fill level,
d) withdrawing the pipetting needle from the liquid, wherein
   if it is determined that the measured fill level exceeds the predefined maximum fill level or is below the predefined minimum fill level, the pipetting needle is withdrawn from the liquid without sucking in a liquid volume, and then steps a) to d) are repeated until it is determined that the measured fill level is below the predefined maximum fill level and exceeds the predefined minimum fill level, and then, before the pipetting needle is withdrawn, the liquid volume to be transferred is sucked in and is thereafter transferred into the second liquid vessel.

The predefined maximum fill level and the predefined minimum fill level are expected parameters or parameters that have been fixed in advance for a given liquid vessel, for example for a sample vessel or a reagent liquid container, or they are calculated from a first fill-level measurement and from a known liquid volume then removed, or they are calculated after a known liquid volume has been discharged into an empty vessel. In the last two cases, a setpoint value of the fill level is usually calculated and a tolerance (+/−) added, as a result of which the maximum fill level and the minimum fill level are predefined.

Preferably, a maximum of ten repeats, particularly preferably a maximum of three, four or five repeats, of steps a) to d) are carried out in immediate succession. It has been noted that this number of repeats already permits the precise removal of liquid from a significantly greater number of liquid vessels for which an implausible fill level had initially been determined.

If it is determined, upon carrying out the maximum number of repeats of steps a) to d), that the measured fill level exceeds the predefined maximum fill level or is below the predefined minimum fill level, the pipetting needle is withdrawn from the liquid, without sucking in a liquid volume, and the first liquid vessel is excluded from further removal of liquid. The affected liquid container can, for example, be identified by an error message which prevents further automatic access, or an alarm can be triggered that indicates the need for the liquid container to be replaced.

If it is determined, upon carrying out the maximum number of repeats of steps a) to d), that the measured fill level exceeds the predefined maximum fill level or is below the predefined minimum fill level, the pipetting needle can alternatively be withdrawn from the liquid, in the final step of the final repeat, without sucking in a liquid volume, and it is not then immersed again into the liquid until a period of at least 5-600 seconds has elapsed, and, after said period of at least 5-600 seconds has elapsed, the pipetting needle is then immersed again into the liquid contained in the first liquid vessel, and the initially described method with the steps of immersion, measurement of the fill level, comparison of the measured fill level with a predefined minimum fill level and a predefined maximum fill level, withdrawal, etc., is repeated. It has been found that a pause between a first and a second number of repeats of steps a) to d) has the effect of permitting the precise removal of liquid from an even greater number of liquid vessels for which an implausible fill level had initially been determined.

In a preferred embodiment, the pipetting needle, during the period of at least 5-600 seconds, can be driven to a wash station, can be washed there and then driven back to the first liquid vessel. In the wash stations provided in automated analysis apparatuses for pipetting needles, the pipetting needle is usually cleaned from the outside and from the inside. This step reduces the risk of an implausible fill-level determination, caused by adherences on the pipetting needle.

Alternatively, the pipetting needle, during the period of at least 5-600 seconds, can be driven to a wash station, can be washed there and then driven to a third liquid vessel. There, the pipetting needle is then immersed into the liquid contained in the third liquid vessel, a liquid volume to be transferred is sucked in, the pipetting needle is withdrawn from the liquid and driven to a fourth liquid vessel into which the liquid volume to be transferred is discharged. The pipetting needle is then driven once again to the wash station, is washed there, and is then driven back to the first liquid vessel. In this case, the pause between a first and a second number of repeats of steps a) to d) during a first transfer of a liquid volume from a first liquid vessel to a second liquid vessel is utilized to carry out a second independent transfer procedure. This has the advantage that a transfer procedure rendered problematic because of an implausible fill level of a liquid vessel does not unnecessarily delay the performance of further necessary transfer procedures, and therefore the desired throughput of the automated analysis apparatus is maintained.

In the method according to the invention for transferring a liquid volume from a first liquid vessel into a second liquid vessel, the first liquid vessel (and the third one) can be a sample vessel, which contains a sample of body fluid for example, or a reagent liquid container, which contains a reagent liquid. The second liquid vessel (and the fourth one) is preferably a reaction vessel or a measurement cell, for example a cuvette or a well in a microtitration plate.

A further subject matter of the present invention is an automated analysis apparatus with at least one pipetting needle which is secured on an automatically displaceable or pivotable transfer arm and which has a fill-level sensor, and with a plurality of receiving positions for receiving liquid vessels, and with a controller which is configured such that it controls a method according to the invention for transferring a liquid volume from a first liquid vessel into a second liquid vessel. The controller is in particular configured such that it controls the following steps:
 a) immersing the pipetting needle into a liquid contained in the first liquid vessel, and measuring the fill level;
 b) comparing the measured fill level with a predefined minimum fill level and a predefined maximum fill level;
 c) determining that the measured fill level
  i. exceeds the predefined maximum fill level or
  ii. is below the predefined maximum fill level and exceeds the predefined minimum fill level or
  iii. is below the predefined minimum fill level,
 d) withdrawing the pipetting needle from the liquid,
 and wherein, if it is determined that the measured fill level exceeds the predefined maximum fill level or is below the predefined minimum fill level, the pipetting needle is withdrawn from the liquid without sucking in a liquid volume, and then steps a) to d) are repeated until it is determined that the measured fill level is below the predefined maximum fill level and exceeds the predefined minimum fill level, and then, before the pipetting needle is withdrawn, the liquid volume to be transferred is sucked in and is thereafter transferred into the second liquid vessel.

In a preferred embodiment, the controller is moreover configured such that a maximum of ten repeats, preferably a maximum of three, four or five repeats, of steps a) to d) are carried out in immediate succession.

In principle, the controller is preferably configured such that it can control all variants and embodiments of the above-described method according to the invention.

In one embodiment of the automated analysis apparatus according to the invention, the apparatus additionally comprises at least one wash station for pipetting needles.

In a further embodiment of the automated analysis apparatus according to the invention, the pipetting needle has a capacitive fill-level sensor.

BRIEF DESCRIPTION OF THE DRAWINGS

An illustrative embodiment of the invention is explained in more detail with reference to drawings, in which.

Identical parts are provided with the same reference signs in all the figures.

DETAILED DESCRIPTION

Figure 1:
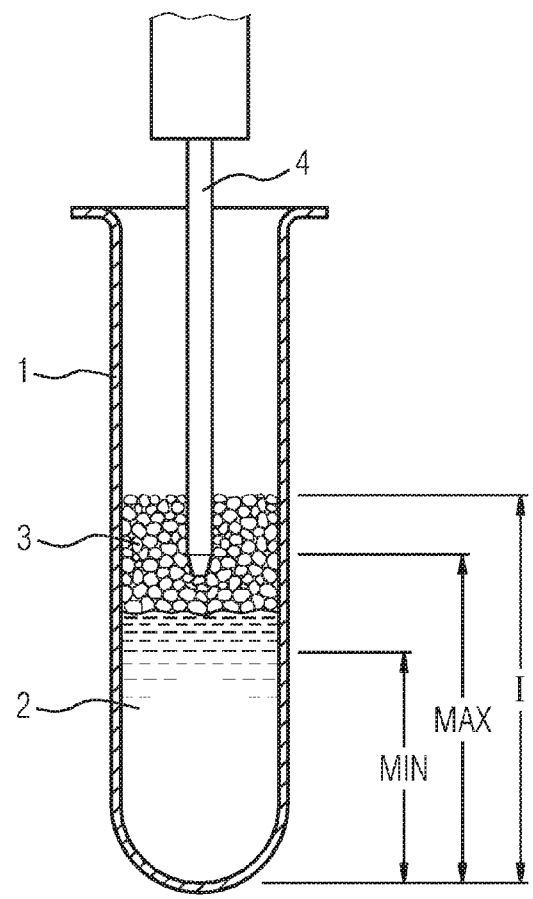
FIG. 1 shows a schematic view of a liquid volume being removed from a liquid vessel.

FIG. 1 shows a schematic view of a sample vessel 1, which contains a sample of human plasma. The sample vessel 1 is situated in an automated analysis apparatus (not shown) which is designed to perform a wide variety of analyses in blood, plasma, serum, urine or other bodily fluids in a fully automated manner, without this requiring action on the part of a user.

A foam layer 3 is situated on the plasma liquid 2. A pipetting needle 4, which is secured on an automatically displaceable transfer arm (likewise not shown) of the analysis apparatus, has been inserted into the sample vessel 1 in order to remove a partial volume of the plasma sample. The pipetting needle 4 has a fill-level sensor (not shown), which detects when the tip of the pipetting needle comes into contact with a liquid surface. In this way, the fill level of the liquid in the liquid vessel can be measured.

In the case shown, a defined quantity of the plasma liquid 2 had been removed, by means of an automated pipetting device, from a primary sample tube (not shown) and had been pipetted into the sample vessel 1. From the known quantity of the transferred plasma liquid 2 and from the known dimensions of the sample vessel 1, a setpoint value for the fill level of the plasma liquid 2 in the sample vessel 1 was calculated by the analysis apparatus. A maximum fill level MAX and a minimum fill level MIN were determined, taking into account a certain tolerance (+/−).

However, in the situation shown here, in which a sub-quantity of the plasma liquid 2 is intended to be removed, a fill level I is determined which exceeds the calculated maximum fill level MAX, because the contact of the pipetting needle tip with the foam 3 is already detected as a contact with a liquid surface. Since the measured fill level I exceeds the permissible maximum fill level MAX, no liquid is sucked in, so as to avoid pipetting inaccuracies. In order nonetheless to permit a precise removal of liquid from the sample vessel 1, the method represented schematically in FIG. 2 is used.

Figure 2:
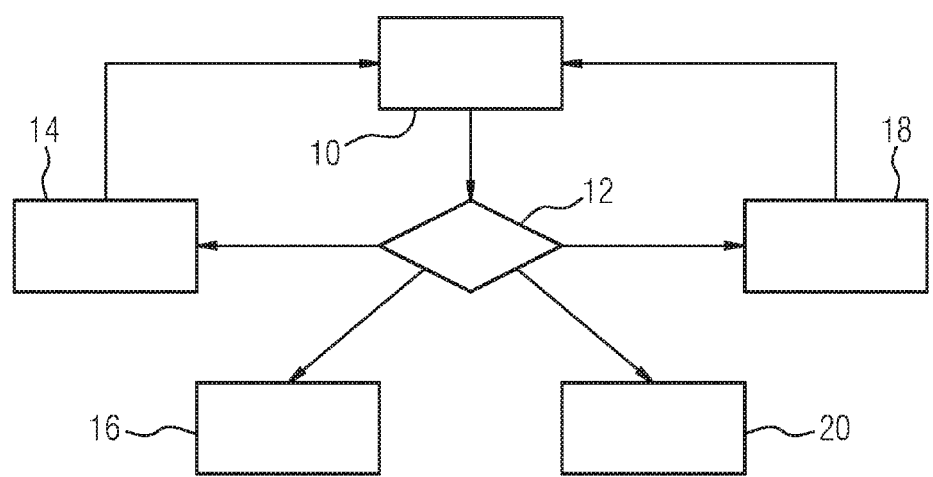
FIG. 2 shows a flow chart of a method for transferring a liquid volume from a first liquid vessel into a second liquid vessel.

FIG. 2 shows a flow chart of a method for automatically transferring a volume of plasma liquid from the sample vessel 1 shown in FIG. 1 into a cuvette. The method is carried out in an automated analysis apparatus comprising, inter alia, a pipetting needle 4 which is secured on a displaceable transfer arm and which has a capacitive fill-level sensor.

In step 10, the pipetting needle 4 is lowered and immersed into the plasma liquid contained in the sample vessel 1, and the fill level I is measured. Moreover, in step 10, the measured fill level I is compared with a predefined minimum fill level MIN and with a predefined maximum fill level MAX. In step 12, a check is made to ascertain whether the measured fill level exceeds the predefined maximum fill level MAX or is below the predefined maximum fill level MAX and exceeds the predefined minimum fill level MIN or is below the predefined minimum fill level MIN. If it is determined in step 12 that the measured fill level I exceeds the predefined maximum fill level MAX or is below the predefined minimum fill level MIN (in this example the maximum fill level MAX is exceeded), the pipetting needle 4 is then withdrawn, in step 14, from the plasma liquid without sucking in a liquid volume, and steps 10, 12 and 14 are repeated, not more than five times, until it is determined in step 12 that the measured fill level I is below the predefined maximum fill level MAX and exceeds the predefined minimum fill level MIN. If such is the case, then, in step 16, the volume of plasma liquid to be transferred is sucked in, and the pipetting needle 4 is withdrawn and then driven to the cuvette into which the volume of plasma liquid is discharged.

If this case, in which a plausible fill level is finally measured in step 12, does not arise, then, in step 18, the pipetting needle 4 is withdrawn from the plasma liquid without sucking in a liquid volume, and it is not immersed again into the liquid until a period of at least 300 seconds has elapsed. After this period has elapsed, steps 10, 12 and 14 are repeated, again not more than five times, until it is determined in step 12 that the measured fill level I is below the predefined maximum fill level MAX and exceeds the predefined minimum fill level MIN.

If, when step 18 has been carried out, the case in which a plausible fill level is finally measured in step 12 does not arise, then, in step 20, the sample vessel 1 is excluded from further removal of liquid, because the risk of incorrect pipetting is too great. For this purpose, the sample vessel 1 is marked with information that prevents automatic access of the pipetting device. The sample vessel 1 is then transferred to a waste container.

LIST OF REFERENCE SIGNS

1 sample vessel
2 plasma liquid
3 foam layer
4 pipetting needle
10-20 method steps
MIN minimum fill level
MAX maximum fill level
I measured fill level

What is claimed is:

1. A method for transferring a liquid volume from a first liquid vessel into a second liquid vessel, wherein a pipetting needle is used which is secured on an automatically displaceable or pivotable transfer arm and which has a fill-level sensor, said method comprising the steps:
   (a) immersing the pipetting needle into the liquid contained in the first liquid vessel, and measuring the fill level;
   (b) comparing the measured fill level with a predefined minimum fill level and a predefined maximum fill level;
   (c) determining that the measured fill level
      i. exceeds the predefined maximum fill level or
      ii. is below the predefined maximum fill level and exceeds the predefined minimum fill level or
      iii. is below the predefined minimum fill level,
   (d) withdrawing the pipetting needle from the liquid, wherein:
   if determined that the measured fill level exceeds the predefined maximum fill level or is below the predefined minimum fill level, the pipetting needle is withdrawn from the liquid without sucking in a liquid volume, and then steps a) to d) are repeated until determined that the measured fill level is below the predefined maximum fill level and exceeds the predefined minimum fill level, and then, before the pipetting needle is withdrawn, the liquid volume to be transferred is sucked in and is thereafter transferred into the second liquid vessel.

2. The method as claimed in claim 1, wherein a maximum of three to ten repeats of steps a) to d) are carried out in immediate succession.

3. The method as claimed in claim 2, wherein if determined, upon carrying out the maximum number of repeats of steps a) to d), that the measured fill level exceeds the predefined maximum fill level or is below the predefined minimum fill level, the pipetting needle is withdrawn from the liquid without sucking in a liquid volume, and the pipetting needle is not immersed again into the liquid until a period of at least 5-600 seconds has elapsed.

4. The method as claimed in claim 3, wherein, after the period of at least 5-600 seconds has elapsed, the pipetting needle is immersed again into the liquid contained in the first liquid vessel, and the method further comprises:
   (e) measuring the fill level;
   (f) comparing the measured fill level with a predefined minimum fill level and a predefined maximum fill level;
   (g) determining that the measured fill level
      i exceeds the predefined maximum fill level or
      ii is below the predefined maximum fill level and exceeds the predefined minimum fill level or
      iii is below the predefined minimum fill level;
   (h) withdrawing the pipetting needle from the liquid;
   wherein if determined that the measured fill level exceeds the predefined maximum fill level or is below the predefined minimum fill level, the pipetting needle is withdrawn from the liquid without sucking in a liquid volume, and then (e) to (h) are repeated until determined that the measured fill level is below the predefined maximum fill level and exceeds the predefined minimum fill level, and then, before the pipetting needle is withdrawn, the liquid volume to be transferred is sucked in and is thereafter transferred into the second liquid vessel.

5. The method as claimed in claim 3, wherein the pipetting needle, during the period of at least 5-600 seconds, is driven to a wash station, is washed there, and is then driven back to the first liquid vessel.

6. The method as claimed in claim 3, wherein the pipetting needle, during the period of at least 5-600 seconds, is driven to a wash station, is washed there, is then driven to a third liquid vessel, is then immersed into the liquid contained in the third liquid vessel, sucks in a liquid volume to be transferred, is withdrawn from the liquid, is driven to a fourth liquid vessel into which the liquid volume to be transferred is discharged, is then driven once again to the wash station, is washed there, and is then driven back to the first liquid vessel.

7. The method as claimed in claim 2, wherein if determined, upon carrying out the maximum repeats of steps a) to d), that the measured fill level exceeds the predefined maximum fill level or is below the predefined minimum fill level, the pipetting needle is withdrawn from the liquid without sucking in a liquid volume, and the first liquid vessel is excluded from further removal of liquid.

8. The method as claimed in claim 1, wherein the first liquid vessel contains a sample liquid or a reagent liquid, and wherein the second liquid vessel is a reaction vessel or a measurement cell.

9. An automated analysis apparatus comprising at least one pipetting needle which is secured on an automatically displaceable or pivotable transfer arm and which has a fill-level sensor, a plurality of receiving positions for receiving liquid vessels, and a controller which is configured such that it controls a method for transferring a liquid volume from a first liquid vessel into a second liquid vessel with the following steps:
- (a) immersing the pipetting needle into a liquid contained in the first liquid vessel, and measuring the fill level;
- (b) comparing the measured fill level with a predefined minimum fill level and a predefined maximum fill level;
- (c) determining that the measured fill level
  - i. exceeds the predefined maximum fill level or
  - ii. is below the predefined maximum fill level and exceeds the predefined minimum fill level or
  - iii. is below the predefined minimum fill level,
- (d) withdrawing the pipetting needle from the liquid, wherein the controller is further configured such that, if determined that the measured fill level exceeds the predefined maximum fill level or is below the predefined minimum fill level, the pipetting needle is withdrawn from the liquid without sucking in a liquid volume, and then steps a) to d) are repeated until determined that the measured fill level is below the predefined maximum fill level and exceeds the predefined minimum fill level, and then, before the pipetting needle is withdrawn, the liquid volume to be transferred is sucked in and is thereafter transferred into the second liquid vessel.

10. The automated analysis apparatus as claimed in claim 9, wherein the controller is further configured such that a maximum of three to ten repeats of steps a) to d) are carried out in immediate succession.

11. The automated analysis apparatus as claimed in claim 10, wherein the controller is further configured such that if determined, upon carrying out the maximum repeats of steps a) to d), that the measured fill level exceeds the predefined maximum fill level or is below the predefined minimum fill level, the pipetting needle is withdrawn from the liquid without sucking in a liquid volume, and the pipetting needle is not immersed again into the liquid until a period of at least 5-600 seconds has elapsed.

12. The automated analysis apparatus as claimed in claim 11, wherein the controller is further configured such that, after the period of at least 5-600 seconds has elapsed, the pipetting needle is immersed again into the liquid contained in the first liquid vessel, and the method for transferring a liquid volume from a first liquid vessel into a second liquid vessel further comprises:
- (e) measuring the fill level;
- (f) comparing the measured fill level with a predefined minimum fill level and a predefined maximum fill level;
- (g) determining that the measured fill level
  - i. exceeds the predefined maximum fill level or
  - ii. is below the predefined maximum fill level and exceeds the predefined minimum fill level or
  - iii. is below the predefined minimum fill level;
- (h) withdrawing the pipetting needle from the liquid;

wherein the controller is further configured such that, if determined that the measured fill level exceeds the predefined maximum fill level or is below the predefined minimum fill level, the pipetting needle is withdrawn from the liquid without sucking in a liquid volume, and then (e) to (h) are repeated until determined that the measured fill level is below the predefined maximum fill level and exceeds the predefined minimum fill level, and then, before the pipetting needle is withdrawn, the liquid volume to be transferred is sucked in and is thereafter transferred into the second liquid vessel.

13. The automated analysis apparatus as claimed in claim 11, further comprising at least one wash station for pipetting needles, wherein the controller is further configured such that the pipetting needle, during the period of at least 5-600 seconds, is driven to the wash station, is washed there, and is then driven back to the first liquid vessel.

14. The automated analysis apparatus as claimed in claim 11, further comprising at least one wash station for pipetting needles, wherein the controller is further configured such that the pipetting needle, during the period of at least 5-600 seconds, is driven to the wash station, is washed there, is then driven to a third liquid vessel, is then immersed into the liquid contained in the third liquid vessel, sucks in a liquid volume to be transferred, is withdrawn from the liquid, is driven to a fourth liquid vessel into which the liquid volume to be transferred is discharged, is then driven once again to the wash station, is washed there, and is then driven back to the first liquid vessel.

15. The automated analysis apparatus as claimed in claim 10, wherein the controller is further configured such that if determined, upon carrying out the maximum repeats of steps a) to d), that the measured fill level exceeds the predefined maximum fill level or is below the predefined minimum fill level, the pipetting needle is withdrawn from the liquid without sucking in a liquid volume, and the first liquid vessel is excluded from further removal of liquid.

16. The automated analysis apparatus as claimed in claim 9, wherein the pipetting needle has a capacitive fill-level sensor.

* * * * *